United States Patent
Takeuchi et al.

(10) Patent No.: US 8,399,418 B2
(45) Date of Patent: Mar. 19, 2013

(54) MONOSEBACATE OF PYRAZOLE DERIVATIVE

(75) Inventors: Hideki Takeuchi, Joetsu (JP); Eiji Tsuru, Joetsu (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 251 days.

(21) Appl. No.: 12/810,476

(22) PCT Filed: Dec. 24, 2008

(86) PCT No.: PCT/JP2008/073405
§ 371 (c)(1),
(2), (4) Date: Jun. 24, 2010

(87) PCT Pub. No.: WO2009/084531
PCT Pub. Date: Jul. 9, 2009

(65) Prior Publication Data
US 2010/0279962 A1    Nov. 4, 2010

(30) Foreign Application Priority Data
Dec. 27, 2007   (JP) ................................. 2007-337985

(51) Int. Cl.
*C07H 17/02* (2006.01)
*A61K 31/7056* (2006.01)
*A61P 3/10* (2006.01)

(52) U.S. Cl. ......................................... 514/27; 536/17.4
(58) Field of Classification Search ........................ None
See application file for complete search history.

(56) References Cited

U.S. PATENT DOCUMENTS

| | | |
|---|---|---|
| 2005/0272669 A1 | 12/2005 | Fushimi et al. |
| 2006/0111560 A1 | 5/2006 | Kumar et al. |
| 2006/0166899 A1 | 7/2006 | Teranishi et al. |

FOREIGN PATENT DOCUMENTS

| | | |
|---|---|---|
| WO | 2004/014932 A1 | 2/2004 |
| WO | 2004/018491 A1 | 3/2004 |
| WO | 2004/019958 A1 | 3/2004 |
| WO | 2005/035517 A1 | 4/2005 |
| WO | 2006/077426 A2 | 7/2006 |
| WO | 2006/097849 A1 | 9/2006 |
| WO | WO 2006/136821 A1 * | 12/2006 |

OTHER PUBLICATIONS

"prevent", WordNet Search—3.0; also available at http://wordnet.princeton.edu/perl/webwn; last viewed May 1, 2012.*
Mayo Clinic Staff, "type 1 diabetes"; also available at http://www.mayoclinic.com/health/type-1-diabetes/DS00329; last viewed May 1, 2012.*

* cited by examiner

*Primary Examiner* — Layla Bland
*Assistant Examiner* — Bahar Craigo
(74) *Attorney, Agent, or Firm* — Sughrue Mion, PLLC

(57) ABSTRACT

The present invention provides a novel form of 3-(3-{4-[3-(β-D-glucopyranosyloxy)-5-isopropyl-1H-pyrazol-4-ylmethyl]-3-methylphenoxy}propylamino)-2,2-dimethylpropionamide with improved storage stability. Since bis[3-(3-{4-[3-(β-D-glucopyranosyloxy)-5-isopropyl-1H-pyrazol-4-ylmethyl]-3-methylphenoxy}propylamino)-2,2-dimethylpropionamide]monosebacate has extremely excellent storage stability, it is useful as a drug substance. Furthermore, it shows an extremely good crystalline property and can be purified by a convenient method, and therefore is suitable for the industrial preparation.

10 Claims, 4 Drawing Sheets

MONOSEBACATE OF PYRAZOLE DERIVATIVE

TECHNICAL FIELD

The present invention relates to a compound (chemical name: bis[3-(3-{4-[3-β(3-D-glucopyranosyloxy)-5-isopropyl-1H-pyrazol-4-ylmethyl]-3-methylphenoxy}-propylamino)-2,2-dimethylpropionamide]monosebacate; hereinafter sometimes to be abbreviated as the "monosebacate") represented by the formula:

[Chem. 1]

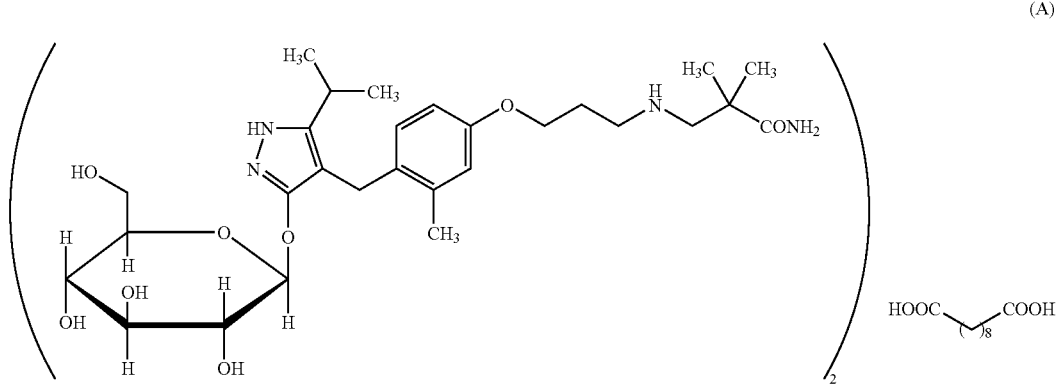

(A)

which exhibits an inhibitory activity in human SGLT1 and is useful as an agent for the prevention or treatment of a disease associated with hyperglycemia such as diabetes, impaired glucose tolerance, impaired fasting glycemia, diabetic complications or obesity, and a disease associated with the increase in blood galactose level such as galactosemia.

BACKGROUND ART

Although a compound as free form represented by the formula:

[Chem. 2]

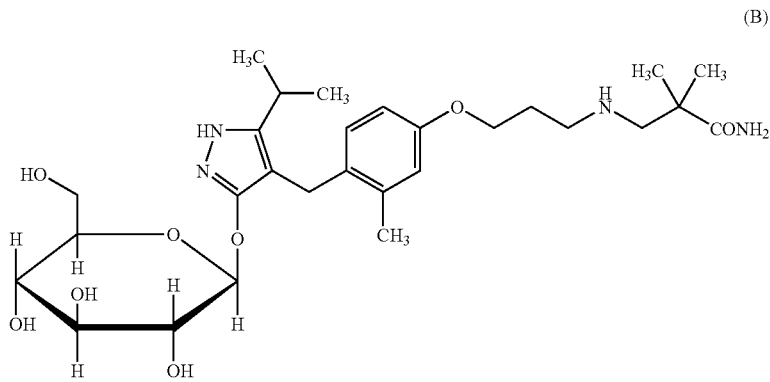

(B)

which exhibits an inhibitory activity in human SGLT1 and is useful as an agent for the prevention or treatment of a disease associated with hyperglycemia such as diabetes, impaired glucose tolerance, impaired fasting glycemia, diabetic complications or obesity, and a disease associated with the increase in blood galactose level such as galactosemia is disclosed (see Patent reference 1), any concrete salts of the compound have not been reported.

Patent reference 1: International publication pamphlet No. 2004/018491

DISCLOSURE OF THE INVENTION

Objects to be Solved by the Invention

The compound (B) described in Patent reference 1 is amorphous. As described in the following Test Example (Storage Stability Test), the decrease in the purity due to decomposition of the compound and the deliquescence were observed. Because of bad storage stability, it is required to make improvement in the physicochemical property to use the compound (B) as a drug substance.

An objective of the present invention is to provide a different form from the above compound (B), which has high storage stability and is usable for a drug substance.

Means of Solving the Objects

The present inventors have earnestly studied to solve the above objective. As a result, the present inventors found that bis[3-(3-{4-[3-(β-D-glucopyranosyloxy)-5-isopropyl-1H-pyrazol-4-ylmethyl]-3-methylphenoxy}propylamino)-2,2-dimethylpropionamide]monosebacate has extremely excellent storage stability and extremely good crystalline property and is suitable for the industrial preparation, and therefore is suitable for a drug substance, thereby accomplished the present invention.

That is, the present invention relates to:

[1] a compound represented by the above chemical structural formula (A);
[2] the compound as described in the above [1], which is crystalline;
[3] the compound as described in the above [2], which has characteristic peaks at diffraction angles (2θ (°)) of 7.6±0.1, 8.5±0.1, 10.6±0.1, 12.8±0.1 and 17.6±0.1 in a diagram of the powder X-ray diffraction;
[4] the compound as described in the above [2], which has an endothermic peak at around 130° C. in a chart of the differential scanning calorimetry;
[5] the compound as described in the above [2], which has characteristic peaks at chemical shift values (δ (ppm)) of 101.4±0.2, 100.9±0.2, 82.8±0.2, 74.2±0.2, 40.9±0.2, 25.5±0.2, 23.1±0.2 and 22.3±0.2 in a chart of the solid-state $^{13}$C-NMR spectrum;
[6] a pharmaceutical composition which comprises as an active ingredient a compound as described in any one of the above [1] to [5];
[7] the pharmaceutical composition as described in the above [6], for the prevention or treatment of a disease associated with hyperglycemia or a disease associated with the increase in blood galactose level;
[8] a medicament which comprises a compound as described in any one of the above [1] to [5] in combination with any one of sulfonylureas and glinides;
[9] the medicament as described in the above [8], which comprises a compound as described in any one of the above [1] to [5] in combination with either gliclazide or mitiglinide calcium hydrate;
[10] the medicament as described in the above [8] or [9], for the prevention or treatment of a disease associated with hyperglycemia; and the like.

Effects of the Invention

The monosebacate of the present invention does not deliquesce in long storage and shows almost no decrease in the purity, and therefore has excellent storage stability. In addition, the monosebacate has an extremely good crystalline property and is excellent in fluidity. Thus, for example, the monosebacate is easy to use for formulation. Furthermore, since the monosebacate can be purified in high purity by a convenient method, it is suitable for the industrial preparation.

BEST MODE FOR CARRYING OUT THE INVENTION

The monosebacate of the present invention can be prepared, for example, by a method described below.

That is, the monosebacate can be prepared by mixing the compound (B) as free form, which can be prepared by a method described in Patent reference 1 or a similar method thereto, and an equal (0.5 equivalents) or a small excess amount of sebacic acid in an appropriate good solvent, dissolving the mixture by heating and optionally adding an appropriate poor solvent thereto, and subsequently isolating and purifying the monosebacate precipitated by cooling to stand, under water cooling or around room temperature.

The good solvents include any solvent which does not interfere with salt formation, and for example, alcohols such as methanol, ethanol, 1-propanol, 2-propanol, 1-butanol, 2-butanol or the like can be used. In addition, the good solvents may be used as a mixture of two or more good solvents.

As the poor solvents which can be suitably added to a good solvent after the salt formation, for example, carboxylic acid esters such as ethyl acetate or the like, hydrocarbons such as heptane, toluene or the like, or ethers such as diisopropyl ether, diethyl ether, tert-butylmethyl ether or the like can be used. In addition, the poor solvents may be used as a mixture of two or more poor solvents.

In the case of using ethanol, 1-propanol, 2-propanol, 1-butanol or 2-butanol as the good solvent, the monosebacate may be precipitated as a solvate crystal on certain occasion. The monosebacate of the present invention can be also prepared by drying the solvate crystal by heating and/or under reduced pressure and removing the solvent appropriately.

The monosebacate of the present invention can be optionally purified by recrystallizing the monosebacate, which is prepared by the above method and the like, using an appropriate recrystallization solvent such as ethanol-diisopropyl ether mixed solvent, ethanol-2-butanol mixed solvent, methanol-diisopropyl ether mixed solvent, methanol-tert-butylmethyl ether mixed solvent, methanol-ethyl acetate mixed solvent, 1-propanol or the like.

The monosebacate of the present invention is useful as an agent for the prevention or treatment of a disease associated with hyperglycemia or a disease associated with the increase in blood galactose level.

In the present invention, as a disease associated with hyperglycemia, diabetes, impaired glucose tolerance, impaired fasting glycemia, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia, gout and the like can be illustrated. In addition, as a disease associated with the increase in blood galactose level, galactosemia and the like can be illustrated.

A pharmaceutical composition of the present invention can be prepared by suitably admixing the monosebacate with a pharmaceutical carrier used conventionally as a pharmaceutical additive such as excipients, disintegrating agents, binders, lubricants, diluents, buffer agents, tonicity agents, antiseptics, moistening agents, emulsifying agents, dispersing agents, stabilizing agents, dissolving aids and the like.

In the case of employing a pharmaceutical composition of the present invention for the practical treatment, various dosage forms can be administered depending upon their usages. As the dosage forms, for example, powders, granules, fine granules, dry syrups, tablets, capsules, injections and the like can be illustrated and they are orally or parenterally administered. The dosage of the monosebacate is appropriately decided depending on the age, sex or body weight of the individual patient, the severity of the disease, the condition to be treated and the like, which is within the range of from about 0.01 mg to about 1000 mg per day per adult human in the case of oral administration and within the range of from about 0.001 mg to about 300 mg per day per adult human in the case of parenteral administration. The daily dose can be divided into one to several doses and administered suitably.

The compound of the present invention can be used in combination with any one of sulfonylureas or glinides. As sulfonylureas, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride and the like can be illustrated. As glinides, nateglinide, mitiglinide calcium hydrate, repaglinide and the like can be illustrated. The dosage of each drug is appropriately decided depending on the age, sex or body weight of the individual patient, the severity of the disease, the condition to be treated and the like according to each effective dose.

In the case of using the compound of the present invention in combination with any one of sulfonylureas or glinides, the present invention includes either dosage forms of simultaneous administration as a single preparation or separated preparations in way of the same or different administration route, and administration at different dosage intervals as separated preparations in way of the same or different administration route. A medicament comprising the compound of the present invention in combination with any one of sulfonylureas or glinides includes both dosage forms as a single preparation and separated preparations for the combination as mentioned above.

EXAMPLES

The present invention is further illustrated in more detail by way of the following Examples and Test Examples. However, the present invention is not limited thereto.

Example 1

Bis[3-(3-{4-[3-(β-D-glucopyranosyloxy)-5-isopropyl-1H-pyrazol-4-ylmethyl]-3-methylphenoxy}propylamino)-2,2-dimethylpropionamide]monosebacate 3-(3-{4-[3-β3-D-Glucopyranosyloxy)-5-isopropyl-1H-pyrazol-4-ylmethyl]-3-methylphenoxy}propylamino)-2,2-dimethylpropionamide (1.00 g) and sebacic acid (0.18 g) were suspended in ethanol (10 mL), and the mixture was dissolved by heating at 70° C. for 5 minutes with stirring. Diisopropyl ether (5 mL) was added to the solution at 70° C., and the mixture was stirred at room temperature for 1 hour. After the precipitates were collected by filtration, the resulting precipitates were dried at 50° C. under reduced pressure, and the title compound (1.05 g) was obtained. Moreover, the resulting compound was dissolved in ethanol (10 mL) by heating under reflux, and diisopropyl ether (5 mL) was added to the solution. After cooling to room temperature, the mixture was stirred overnight. After the precipitated crystals were collected by filtration and dried at 50° C. under reduced pressure, the purified crystals of the title compound (0.96 g) were obtained.

$^1$H-NMR (DMSO-$d_6$) (δ (ppm)): 1.00-1.10 (12H, m), 1.24 (4H, s), 1.40-1.50 (2H, m), 1.70-1.90 (2H, m), 2.17 (2H, t, J=7.0 Hz), 2.26 (3H, s), 2.64 (2H, t, J=6.5 Hz), 2.70-2.80 (1H, m), 3.00-3.20 (4H, m), 3.40-3.50 (3H, m), 3.62 (1H, d, J=11.5 Hz), 3.93 (2H, t, J=6.0 Hz), 4.20-4.80 (1H, br), 5.18 (1H, d, J=8.0 Hz), 6.60 (1H, d, J=8.0 Hz), 6.69 (2H, s), 6.82 (1H, d, J=8.5 Hz), 7.47 (1H, s)

The powder X-ray diffraction, differential scanning calorimetry, infrared absorption spectroscopy and solid-state $^{13}$C-NMR spectrum of the resulting monosebacate crystals were measured under the following conditions and respective data were obtained.

The powder X-ray diffraction was measured using RINT2100 Powder X-ray diffractometer (Rigaku, Analytical condition: Cu Kα radiation, 40 kV in tube voltage, and 40 mA in tube current). The resulting diffraction diagram is shown in FIG. 1, and diffraction angles 2θ (°) and relative intensities (%) of main peaks are shown in Table 1.

TABLE 1

| diffraction angle | relative intensity |
|---|---|
| 6.7 | 22 |
| 7.6 | 93 |
| 8.5 | 61 |
| 10.6 | 90 |
| 12.2 | 44 |
| 12.8 | 100 |
| 17.0 | 47 |
| 17.6 | 63 |
| 18.5 | 48 |
| 24.5 | 38 |

The differential scanning calorimetry was measured using Thermo plus DSC8230 differential scanning calorimeter (Rigaku, Sample amount for measurement: 5.35 mg, Heating rate: 10° C./min, Reference material: alumina). The resulting chart is shown in FIG. 2.

Endothermic peak: 129.7° C.

The infrared absorption spectrum was measured using AVATAR320 (Thermo Electron) by potassium bromide disk method. The resulting spectrum chart is shown in FIG. 3.

Characteristic wave numbers of infrared absorption peaks ($cm^{-1}$): 3240, 2930, 1670, 1560, 1500, 1400, 1290, 1250 and 1070

The solid-state $^{13}$C-NMR spectrum was measured using Avance DRX500 (Bruker) at the rate of 10 kHz by CP/MAS method, after the test sample was filled up in a zirconia rotor (internal diameter: 4 mm). The resulting spectrum chart is shown in FIG. 4.

Chemical shift values of the solid-state $^{13}$C-NMR (δ (ppm)): 180.8, 158.9, 157.0, 148.3, 138.2, 134.3, 131.2, 119.7, 109.2, 101.4, 100.9, 82.8, 76.5, 74.2, 69.4, 57.2, 54.7, 54.4, 40.9, 25.5, 23.1 and 22.3

Example 2

Bis[3-(3-{4-[3-(β-D-glucopyranosyloxy)-5-isopropyl-1H-pyrazol-4-ylmethyl]-3-methylphenoxy}propylamino)-2,2-dimethylpropionamide]monosebacate 3-(3-{4-[3-(β-D-Glucopyranosyloxy)-5-isopropyl-1H-pyrazol-4-ylmethyl]-3-methylphenoxy}propylamino)-2,2-dimethylpropionamide (20.25 g) and sebacic acid (3.63 g) were suspended in 1-propanol (210 mL). After the mixture was dissolved by heating at 65° C. with stirring, the solution was stirred for 10 minutes. The mixture was cooled in a container with water bath, and was stirred at room temperature overnight. The precipitated crystals were collected by filtration and were dried under reduced pressure at room temperature for 2 hours and at 50° C. for 2 hours, and the crystals of the title compound (22.9 g) were obtained. As a result of the powder X-ray diffraction analysis, the resulting crystals showed a similar diffraction pattern to that of Example 1.

Test Example 1

Storage Stability Test

The crystals of the monosebacate in Example 1 and amorphous 3-(3-{4-[3-(β-D-glucopyranosyloxy)-5-isopropyl-1H-pyrazol-4-ylmethyl]-3-methylphenoxy}propylamino)-2,2-dimethylpropionamide (free form) as Comparative Example were stored under condition of 40° C./75% relative humidity or 60° C. in open vessels, existence or nonexistence of the deliquescence and the storage stability for 2 months were examined. Concerning the storage stability, the purity of each test compound was measured by HPLC at initial and after storage for 2 months, and these results were compared. Analytical conditions of HPLC are as follows.

Analytical Conditions

Detector: ultraviolet-visible absorption spectrophotometer

Wave length: 225 nm

Column: LUNA C18(2) (produced by Phenomenex), 5 μm, 4.6×250 mm, particle diameter $100 \times 10^{-10}$ m Column Temperature: a constant temperature of around 25° C.

Sample concentration: 1 mg/mL

Injection volume: 10 μL

Flow rate: 1.2 mL/min

Mobile phase A: 10 mM dipotassium hydrogenphosphate aqueous solution adjusted to pH 7.8 with phosphoric acid Mobile phase B: Acetonitrile Rate of mobile phases:

0-30 min: Mobile phase A/Mobile phase B=78/22, 30-50 min: Mobile phase A/Mobile phase B=78/22→30/70, 50-60 min: Mobile phase A/Mobile phase B=30/70

Range of area measurement: for 50 minutes from the start, except for the area of the peak of the blank solution The results of the test under the storage condition of 40° C./75% relative humidity are as shown in Table 2. The deliquescence from the initial of the experiment and the decrease in the purity were observed in free form under the above condition. On the other hand, the monosebacate of the present invention had excellent storage stability.

TABLE 2

| Measurement | Example 1 The monosebacate (crystals) | | Comparative Example Free form (amorphous) | |
|---|---|---|---|---|
| point | Initial | After 2 months | Initial | After 2 months |
| Purity (%) | 99.6 | 99.5 | 98.7 | 97.0 |
| Deliquescence | | Nil | | Yes |

The results of the test under the storage condition of 60° C. in open vessels are as shown in Table 3. The remarkable decrease in the purity due to the decomposition was observed in free form under the high temperature environment. On the other hand, the monosebacate of the present invention showed almost no decrease in the purity and had excellent storage stability.

TABLE 3

| Measurement | Example 1 The monosebacate (crystals) | | Comparative Example Free form (amorphous) | |
|---|---|---|---|---|
| point | Initial | After 2 months | Initial | After 2 months |
| Purity (%) | 99.6 | 99.2 | 98.7 | 95.3 |

As described above, like the results of Tables 2 and 3, the monosebacate of the present invention has extremely excellent storage stability. Thus, the monosebacate is an excellent compound which can solve a problem of the physicochemical properties such as the decrease in the purity and deliquescence in free form.

Test Example 2

Oral Glucose Tolerance Test (1) Combination Effect with Sulfonylureas

Male Wistar rats (Charles River Japan, Inc.) at 9 weeks of age, fasted about 16 hours (each group has 6 animals), were administrated orally in a volume of 2.5 mL/kg with distilled water and 0.1% methylcellulose solution in the Control group, with the monosebacate (0.03 mg/kg as the above compound (B) (free form)) dissolved in distilled water (hereinafter referred to as the "monosebacate solution") and 0.1% methylcellulose solution in the Monosebacate alone group, with gliclazide (0.3 mg/kg as gliclazide) dissolved in 0.1% methylcellulose solution (hereinafter referred to as the "gliclazide solution") and distilled water in the Gliclazide alone group and with the monosebacate solution and the gliclazide solution (0.03 mg/kg as the compound (B) and 0.3 mg/kg as gliclazide) in the Gliclazide combination group, respectively. Subsequently, 0.4 g/mL of glucose solution (5 mL/kg) was loaded orally. The blood was collected from tail vein before and 1 hr after administration of test substance, and the plasma glucose concentrations were measured using Glucose C-II test WAKO (Wako Pure Chemical Industries, Ltd.). The results are illustrated in Table 4. The numerical values in the table represent mean value±standard error. In both the Monosebacate alone group and the Gliclazide alone group, lower plasma glucose concentrations at 1 hr after the administration were seen as compared with the Control group. In the Gliclazide combination group, much lower plasma glucose concentration was seen.

TABLE 4

| | Plasma glucose concentration (mg/dL) | |
|---|---|---|
| Group | Just before administration | 1 hr after administration |
| The Control group | 84.9 ± 1.9 | 152.1 ± 7.0 |
| The Monosebacate alone group | 81.6 ± 3.1 | 127.6 ± 3.8 |
| The Gliclazide alone group | 80.7 ± 6.7 | 136.5 ± 6.7 |
| The Gliclazide combination group | 84.4 ± 3.8 | 110.2 ± 6.2 |

(2) Combination Effect with Glinides

Instead of gliclazide in the Gliclazide alone group and the Gliclazide combination group, mitiglinide calcium hydrate (JAN) (0.3 mg/kg as mitiglinide calcium hydrate) was used (hereinafter referred to as the "Mitiglinide alone group" and the "Mitiglinide combination group", respectively), and the plasma glucose concentrations were measured in the same way as the above method (1). The results are illustrated in Table 5. The numerical values in the table represent mean value±standard error. In both the Monosebacate alone group and the Mitiglinide alone group, lower plasma glucose concentrations at 1 hr after the administration were seen as compared with the Control group. In the Mitiglinide combination group, much lower plasma glucose concentration was seen.

TABLE 5

| | Plasma glucose concentration (mg/dL) | |
|---|---|---|
| Group | Just before administration | 1 hr after administration |
| The Control group | 86.8 ± 0.9 | 164.9 ± 2.4 |
| The Monosebacate alone group | 83.8 ± 1.8 | 141.3 ± 5.6 |
| The Mitiglinide alone group | 85.8 ± 1.7 | 119.1 ± 5.8 |
| The Mitiglinide combination group | 83.0 ± 2.4 | 114.0 ± 1.6 |

INDUSTRIAL APPLICABILITY

The monosebacate of the present invention has excellent storage stability and other physicochemical properties. Therefore, it is useful as a drug substance and is suitable for the industrial preparation.

Figure 1:
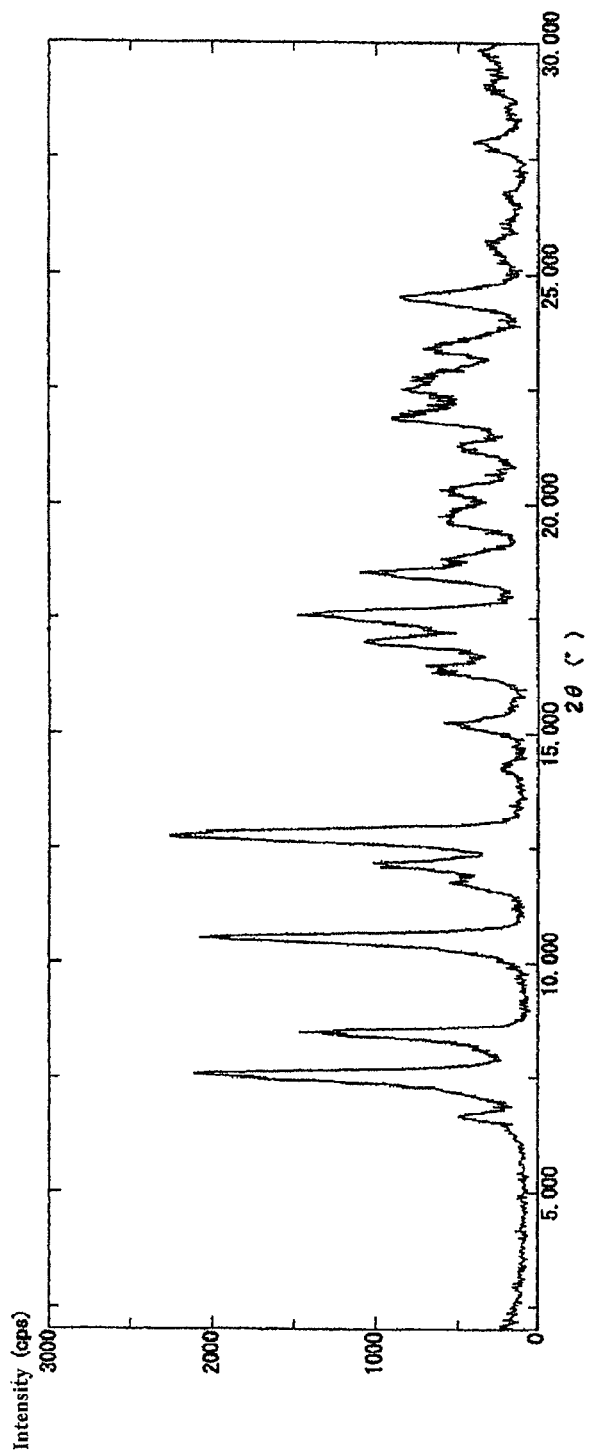
FIG. 1 is a diagram of the powder X-ray diffraction of the monosebacate obtained in Example 1. The axis of ordinate shows diffraction intensity of X-rays (cps), and the axis of abscissas shows diffraction angle (2θ).
Figure 2:
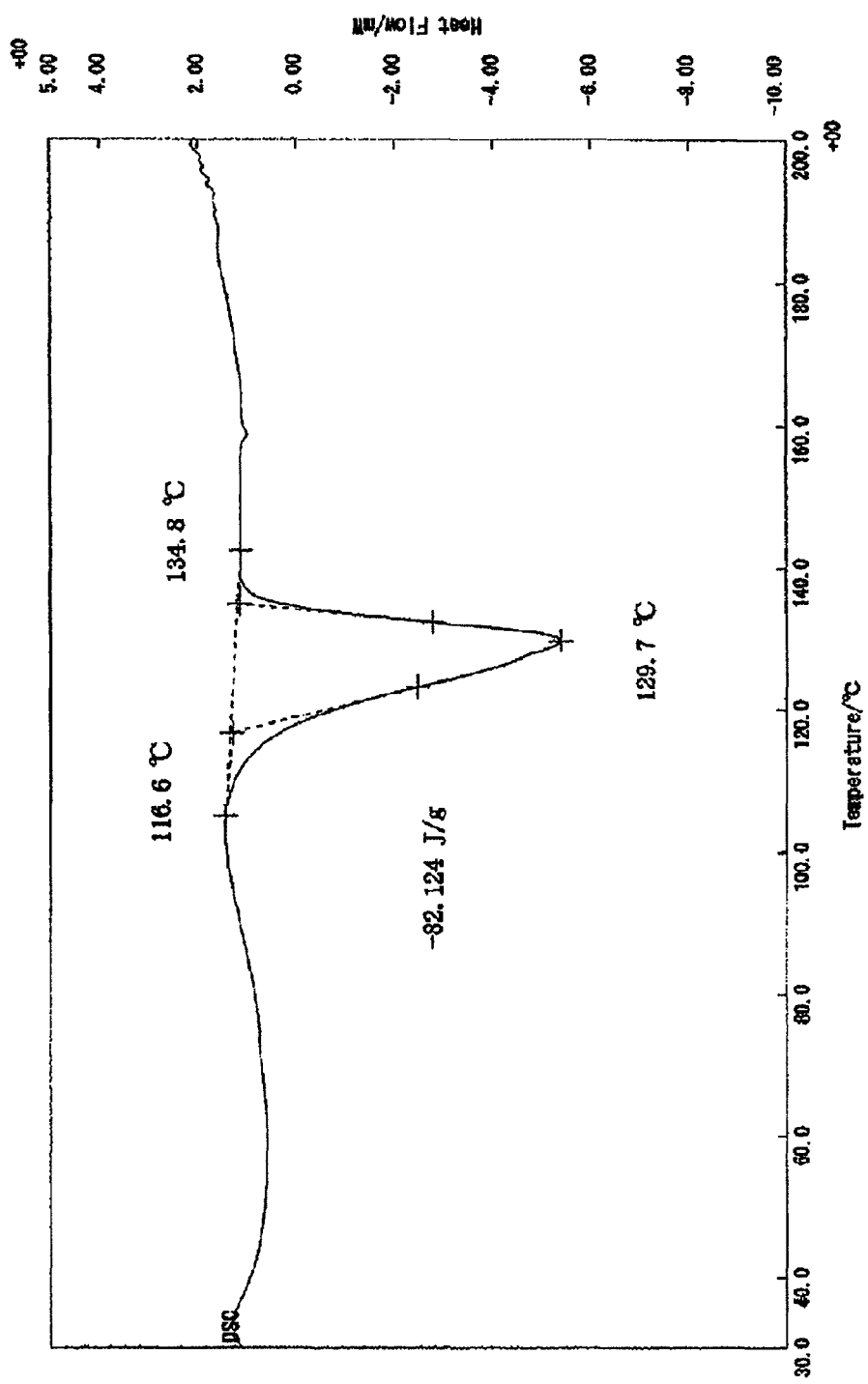
FIG. 2 is a chart of the differential scanning calorimetry of the monosebacate obtained in Example 1. The axis of ordinate shows heat flow (mW), and the axis of abscissa shows temperature (° C.).
Figure 3:
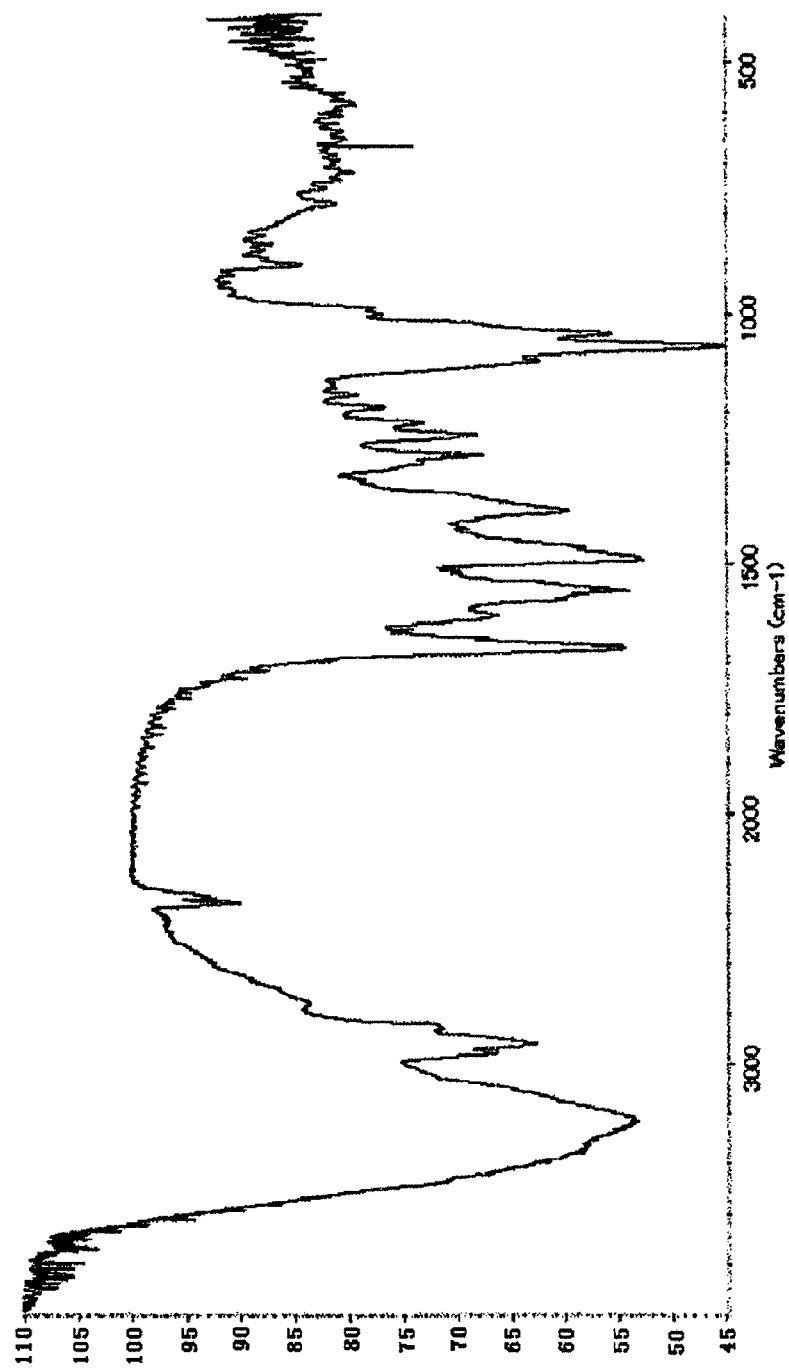
FIG. 3 is a chart of the infrared absorption spectrum of the monosebacate obtained in Example 1. The axis of ordinate shows transmittance (% T), and the axis of abscissa shows wave number (cm$^{-1}$).
Figure 4:
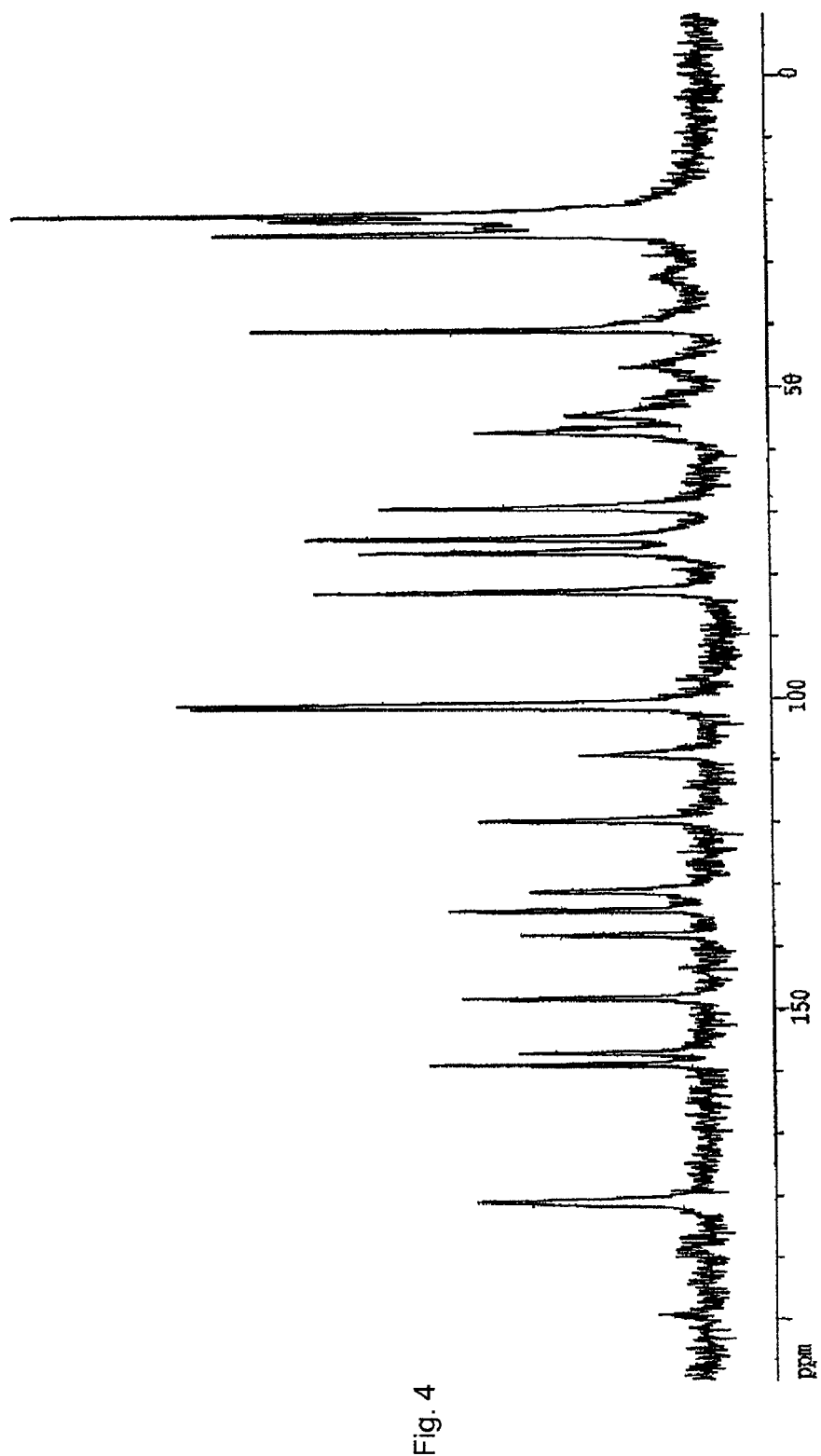
FIG. 4 is a chart of the solid-state $^{13}$C-NMR spectrum of the monosebacate obtained in Example 1. The axis of ordinate shows intensity, and the axis of abscissa shows chemical shift value (δ(ppm)).

The invention claimed is:

1. A compound represented by the structural formula:

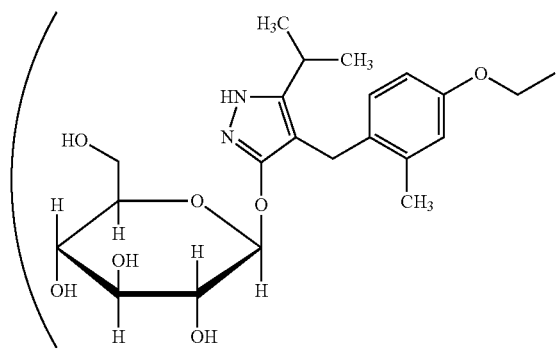

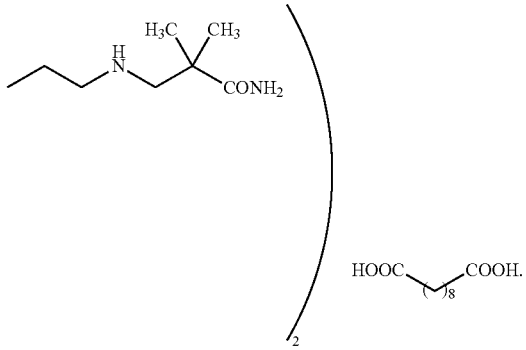

2. The compound as claimed in claim 1, which is crystalline.

3. The compound as claimed in claim 2, which has characteristic peaks at diffraction angles (2θ (°)) of 7.6±0.1, 8.5±0.1, 10.6±0.1, 12.8±0.1 and 17.6±0.1 in a diagram of the powder X-ray diffraction.

4. The compound as claimed in claim 2, which has an endothermic peak at around 130° C. in a chart of the differential scanning calorimetry.

5. The compound as claimed in claim 2, which has characteristic peaks at chemical shift values (δ (ppm)) of 101.4±0.2, 100.9±0.2, 82.8±0.2, 74.2±0.2, 40.9±0.2, 25.5±0.2, 23.1±0.2 and 22.3±0.2 in a chart of the solid-state $^{13}$C-NMR spectrum.

6. A pharmaceutical composition which comprises as an active ingredient a compound as claimed in claim 1.

7. The pharmaceutical composition as claimed in claim 6, for the treatment of a disease associated with hyperglycemia or a disease associated with the increase in blood galactose level.

8. A medicament which comprises a compound as claimed in claim 1 in combination with any one of sulfonylureas and glinides.

9. The medicament as claimed in claim 8, in combination with either gliclazide or mitiglinide calcium hydrate.

10. The medicament as claimed in claim 8, for the treatment of a disease associated with hyperglycemia.

* * * * *